(12) United States Patent
Fayeulle et al.

(10) Patent No.: US 6,915,685 B2
(45) Date of Patent: Jul. 12, 2005

(54) TOOL HOLDER FOR MEASUREMENT MEANS

(75) Inventors: Emmanuel Fayeulle, Paris (FR); Laure Mandrou, Courbevoie (FR); Philippe Salamitou, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/477,634

(22) PCT Filed: Apr. 26, 2002

(86) PCT No.: PCT/EP02/04658

§ 371 (c)(1),
(2), (4) Date: Apr. 23, 2004

(87) PCT Pub. No.: WO02/093146

PCT Pub. Date: Nov. 21, 2002

(65) Prior Publication Data

US 2004/0173016 A1 Sep. 9, 2004

(30) Foreign Application Priority Data

Mar. 11, 2001 (FR) ............................................ 01/06344

(51) Int. Cl.⁷ ................................................ E21B 49/08
(52) U.S. Cl. .................................................. 73/152.42
(58) Field of Search ........................ 73/152.42, 152.18; 250/356.1, 269.3

(56) References Cited

U.S. PATENT DOCUMENTS

| | | | | |
|---|---|---|---|---|
| 2,953,681 A | * | 9/1960 | Frazier .................... | 250/356.1 |
| 3,202,822 A | * | 8/1965 | Kehler ........................ | 250/266 |
| 4,760,252 A | * | 7/1988 | Albats et al. .......... | 250/390.07 |
| 4,974,446 A | * | 12/1990 | Vigneaux ................. | 73/152.42 |
| 5,005,194 A | | 4/1991 | Fritz et al. | |
| 5,025,160 A | * | 6/1991 | Watt ......................... | 250/356.1 |
| 5,361,632 A | | 11/1994 | Magnani | |
| 5,479,020 A | | 12/1995 | Mohn | |
| 5,539,225 A | * | 7/1996 | Loomis et al. ........... | 250/269.4 |
| 5,608,215 A | * | 3/1997 | Evans ....................... | 250/269.6 |
| 5,804,820 A | * | 9/1998 | Evans et al. ............. | 250/269.6 |
| 6,265,713 B1 | * | 7/2001 | Berard et al. ............. | 250/269.3 |
| 6,504,604 B1 | * | 1/2003 | Holland ..................... | 356/73.1 |
| 6,703,606 B2 | * | 3/2004 | Adolph ..................... | 250/269.1 |
| 2002/0170348 A1 | * | 11/2002 | Roscoe et al. ........... | 73/152.02 |

FOREIGN PATENT DOCUMENTS

| | | | | |
|---|---|---|---|---|
| DE | 37 23 437 | | 6/1988 | |
| DE | 3723437 A1 | * | 6/1988 | ............ G01N/9/24 |
| EP | 269432 A2 | * | 6/1988 | .......... G01N/23/12 |
| WO | WO 94 25859 | | 11/1994 | |
| WO | WO 9425859 A1 | * | 11/1994 | .......... G01N/23/12 |

* cited by examiner

Primary Examiner—Hezron Williams
Assistant Examiner—John Fitzgerald
(74) Attorney, Agent, or Firm—Victor H. Segura; Brigitte L. Echols

(57) ABSTRACT

The invention relates to a tool holder serving to receive measurement means (9, 10, 13) for characterizing a multi-phase fluid coming from a deposit (17) through which at least one well (16) passes, and flowing inside said tool holder. According to the invention, the tool holder is provided with an axial cavity (3) and with a first radial opening (4) which opens out in the inside wall of said tool holder and intercepts said axial cavity, said cavity and said opening serving to receive said measurement means. The invention also relates to a device for characterizing a multi-phase fluid coming from a deposit (17) through which at least one well (16) passes, said device comprising: a source unit (9) for emitting gamma rays through said multi-phase fluid, and a detector unit (10) having a scintillator crystal (10a) receiving said gamma rays after they have passed through the fluid. According to the invention, said device further comprises a tool holder (1) of the invention, and the detector unit (10) is positioned in the axial cavity (3) of said tool holder so that the scintillator crystal (10a) is situated in the first radial opening (4) in said tool holder.

20 Claims, 2 Drawing Sheets

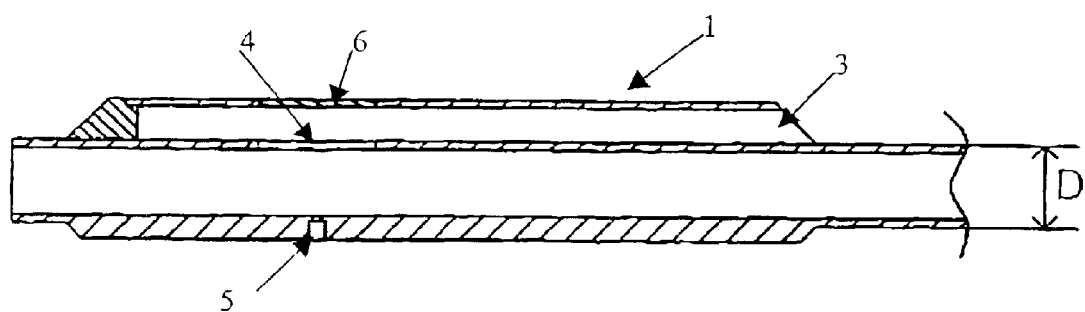
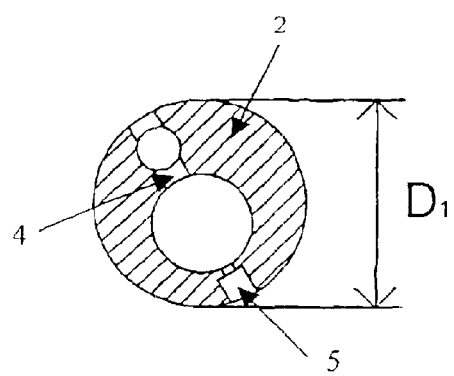
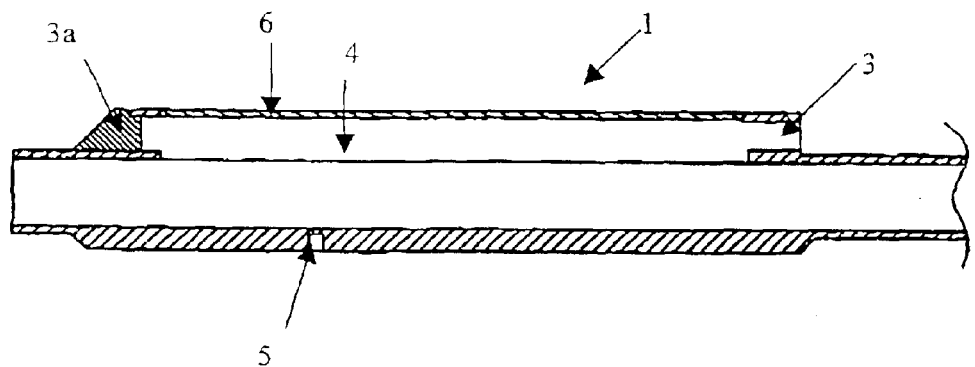

TOOL HOLDER FOR MEASUREMENT MEANS

The invention relates to a tool holder for measurement means, and more particularly to a tool holder for receiving measurement means making it possible to characterize a multi-phase fluid coming from a deposit through which at least one well passes. The invention also relates to a device for characterizing a multiphase fluid coming from a deposit, said device comprising a a tool holder of the invention and measurement means making it possible to determine the density and the multi-phase ratio of said fluid.

The capacity of the petroleum industry to optimize production from a deposit is dependent on it being possible to evaluate continuously the quantity (flow rate) and the composition (proportions of the various phases) of the effluent output from the well. Conventional practice in the petroleum industry for characterizing the composition of multi-phase effluents consists in separating the effluent into its component phases, and in measuring the resulting separated phases. But in that technique, separators must be put in place on site, and such equipment is costly and voluminous. And also, when doing well testing, additional pipes must be put in place.

Numerous proposals have been put forward for developing techniques that avoid the need for such separators. Such developments are described in Publication SPE 28515 (SPE Annual Technical Conference, New Orleans, Sep. 25–28, 1994) by J. Williams, entitled "Status of Multiphase Flow Measurement Research".

Among those solutions, it is known that a device can be used that comprises a source which emits gamma rays through the effluent in order to determine its multi-phase ratio and its density, the attenuation of said rays being measured by a detector unit situated facing the source unit. Document U.S. Pat. No. 5,361,632 describes a device for characterizing an effluent by using a gradiomanometer and a gamma ray densimeter. Unfortunately, that device is ineffective in wells that are close to the horizontal In addition, since such a device obstructs the well, it cannot be installed permanently.

Document PCT/GB00/01758 describes a device for measuring the density and the multi-phase ratio of the fluid. That device makes it possible to obtain better results regardless of the types of well tested, and it is capable of being installed permanently down the well. That device comprises a tool holder constituting a segment of a production tube located down a well that passes through at least one deposit of multi-phase fluid. That tool holder receives a gamma ray source unit and a detector unit. The source unit and the detector unit are installed on diametrically-opposite outside walls of the tool holder. The effluent to be characterized thus passes through the inside of the tool holder and it is intercepted by the beam of gamma rays sent by the source unit, and the attenuation of the rays is then measured by the detector unit. In spite of it being ingenious, that device does suffer from some drawbacks. Optimum accuracy is not obtained in measuring the attenuation of the gamma rays, in particular due to the positioning of the source unit and of the detector unit. Since the units are installed on the outside walls of the tool holder, the gamma rays coming from the source unit must firstly pass through the thickness of the tool holder—and they are therefore subjected to initial interference attenuation—and then they must go back through said tool holder—thereby being subjected to subsequent interference attenuation—in order to be detected by the detector unit. The counts performed by the detector unit are thus disturbed significantly by the initial and subsequent interference attenuation suffered by the gamma rays.

It would therefore be particularly advantageous to provide a tool holder in which the means for receiving the measurement means, in particular for receiving a source unit and a detector unit, make it possible to minimize the interference attenuation of the gamma rays. This can be achieved by bringing the source and the scintillator crystal of the detector directly closer to the inside walls of the tool, e.g. by installing them directly in contact with the flow of fluid to be characterized However, numerous constraints must be satisfied by the tool holder, which must first and foremost be strong enough to withstand high pressures, in particular the differential pressure prevailing between the inside and the outside of the tool. The tool holder must also be leaktight because the multi-phase fluid flows through it, while the measurement tools must be connected to electronic means that convey the data back to the surface, and that are generally situated on the outside wall of said tool holder: there must not be any disturbance to the flow rate desired for the multi-phase fluid at the surface; therefore there must not be any leaks between the outside and the inside of the tool holder.

An object of the invention is thus to provide a tool holder that makes it possible to improve the results obtained when characterizing a multiphase fluid, while still satisfying the conditions required by the strength and sealing constraints, in particular when it is used down a well bored through geological formations.

To this end, the invention provides a tool holder serving to receive measurement means for characterizing a multiphase fluid coming from a deposit through which at least one well passes, and flowing inside said tool holder. According to the invention, the tool holder is provided with an axial cavity and with a first radial opening which opens out in the inside wall of said tool holder and intercepts said axial cavity, said cavity and said opening serving to receive said measurement means.

In this way, the axial cavity makes it possible to receive part of the measurement tools without weakening the tool holder, and the radial opening makes it possible to bring the detection means of the measurement tools closer to the effluent, and thus to reduce interference attenuation generated by the disposition of the detection means in state-of-the-art devices. In addition, the simplicity of the way in which the cavity and the openings are arranged makes it possible for the tool holder to be sealed simply and effectively. Finally, it is not necessary to manufacture special tool holders in order to obtain these advantageous effects, it being sufficient merely to modify existing tool holders, which limits the cost of the solution of the invention.

In an advantageous embodiment of the invention, the tool holder is further provided with a second radial opening which opens out in the inside wall of the tool holder and is diametrically opposite from the first radial opening.

In particular when the measurement means include a source unit serving to send gamma rays through the effluent towards a detector unit, this solution makes it possible firstly to bring the detector unit (situated in the first radial opening) closer to said effluent, and secondly to bring the source unit (situated in the second radial opening) closer to said effluent. In this way, in combination with the radial opening receiving the detector unit, the tool holder of the invention makes it possible to reduce all of the interference attenuation due to the walls of state-of-the-art tool holders.

In a preferred embodiment of the invention, the first radial opening also opens out in the outside wall of the tool holder, and it is sealed off by a stopper situated on said outside wall.

In this embodiment, the radial opening is formed merely by radial boring from the outside wall of the tool holder. This embodiment is preferred because the machining it requires is very practical and inexpensive. In which case, in order to make the tool holder leaktight, it is necessary merely to place a stopper on its outside wall.

The invention also provides a device for characterizing a multi-phase fluid coming from a deposit through which at least one well passes, said device comprising:

a source unit for emitting gamma rays through said multi-phase fluid; and a detector unit having a scintillator crystal.

According to the invention, the characterizing device further comprises a tool holder as proposed above, and the detector unit is positioned in the axial cavity of said tool holder so that the scintillator crystal is situated in the first radial opening in said tool holder.

Advantageously, the first radial opening is an oblong opening whose dimensions correspond to the dimensions of the scintillator crystal. This makes it possible for the bores in the tool holder to be "just large enough." Thus, the results delivered by the measurement means are optimized—it is particularly important for the crystal to be directly in contact with the fluid to be characterized—while minimizing the weakening of the tool holder, in order to guarantee the strength thereof.

Other advantages and characteristics of the invention are highlighted in the following description given with reference to the accompanying drawings, in which:

FIGS. 1a and 1b-are section-views of an embodiment of a tool holder of the invention;

FIG. 1c is a section view of another embodiment of a tool holder of the invention;

FIG. 2a is a detail of an embodiment of a device of the invention for characterizing a fluid.

Figure 2:
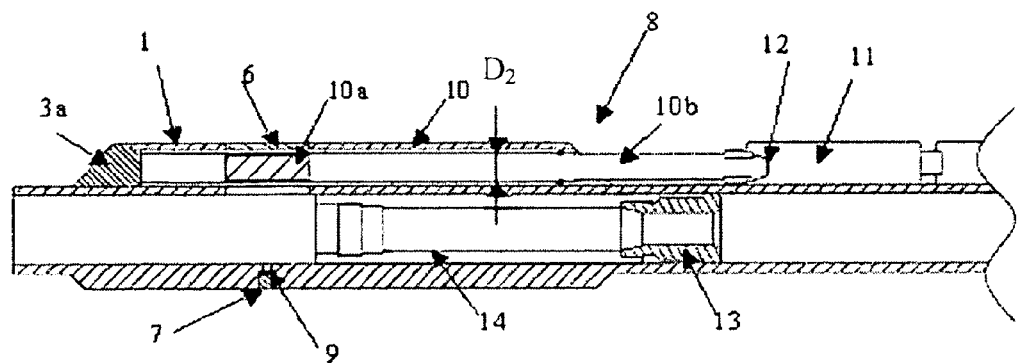
FIG. 2 is a section view of an embodiment of a device of the invention for characterizing a fluid.

FIGS. 1a and 1c show two embodiments of a tool holder 1 of the invention. As can be seen in FIG. 1b which shows a section through the embodiment shown in FIG. 1a, the body of the tool holder 1 is substantially cylindrical in shape with, over a portion of its length, an eccentric segment 2, i.e. a portion in which the outside diameter $D_1$ of the tool holder 1 is greater than the outside diameter D of the remainder of said tool holder, while the inside diameters remain identical. The eccentric segment is also present in the embodiment shown in FIG. 1c. However, this shape is not limiting to the invention, and the tool holder may have any shape suitable for receiving measurement means.

The eccentric segment 2 is provided with an axial cavity 3 over substantially its entire length. The axial cavity 3 is preferably provided where the thickness of the eccentric segment 2 is greatest, in order to minimize weakening the body of the tool holder. But as can be seen in FIG. 1b, depending on the conditions under which the tool holder is used, the axial cavity 3 may be provided in any thickness of the eccentric segment provided that its dimensions are suitable for ensuring that the tool holder retains sufficient strength. Since the cavity 3 extends along the entire length of the eccentric segment 2, its end which is opposite from the end receiving the measurement means is sealed off by sealing means 3a known in the state of the art.

The diameter of the axial cavity is dimensioned so as to minimize the extent to which it weakens the eccentric segment 2 of the tool holder, while making it possible to receive measurement means of usual dimensions, and whose diameter is referenced $D_2$. The dimensions of the cavity depend firstly on the material from which the tool holder is made and secondly on the technique used for subsequent insertion of the measurement means, in particular of the detector unit, as explained below with reference to FIG. 2. There are two possible ways of installing said means:

the measurement means are inserted from the outside of the tool holder, as in the embodiment shown in FIGS. 1a and 1b; or the measurement means are inserted from the inside of the tool holder, as in the embodiment shown in FIG. 1c.

With reference to FIGS. 1a and 1b:

The diameter of the axial cavity is totally contained within the thickness of the eccentric segment 2. Therefore, in order to position the measurement means in contact with the fluid flowing through the body of the tool holder, it is necessary to form a first radial opening 4 in the inside wall of the tool holder, and intercepting the axial cavity 3. A second radial opening 5 opens out into the inside wall of the tool holder, diametrically opposite from the first radial opening 4. As explained in more detail with reference to FIG. 2, the two radial openings make it possible to install a gamma ray source and a scintillator crystal of a detector unit so that they face each other in order to characterize a fluid flowing through the tool holder. The fact that the openings 4 and 5 open out in the inside wall of the tool holder thus makes it possible to bring the measurement means closer to the fluid to be characterized, and thus to minimize all of the interference attenuation that is generated by tool holders in the state of the art.

Advantageously, a window made of materials that offer low gamma ray attenuation (e.g. poly-ether-ether-ketone (PEEK), a thermoplastic resin) may be provided in the inside wall of the tool holder at each of the radial openings 4 and 5. Such a window makes it possible to avoid any fluid or debris stagnating in the space extending between the inside wall of the tool holder and the walls of the measurement means. In the embodiment of the invention, the radial openings 4 and 5 are formed merely by radial boring from the outside wall of the tool holder. This solution is advantageous because it is very easy and therefore inexpensive to achieve. In which case, in order to guarantee that the tool holder is leaktight, leaktight stoppers 6 and 7 are provided respectively for the radial opening 4 and for the radial opening 5. The radial openings 4 and 5 may also be formed by tools inserted inside the tool holder 1. In which case, said radial openings do not open out in the outside wall of said tool holder, and it is not necessary to provide stoppers 6 and 7. However, this solution requires machining that is more complex.

The solution shown with reference to FIGS. 1a and 1b is therefore advantageous not only because it is particularly easy to install the measurement means from the outside of the tool holder, but also because said means are then easily accessible, and they are therefore easy to remove for the purposes of repair or the like. However, since it requires a radial opening 4 to be bored that intercepts the axial cavity 3, this solution weakens the tool holder. Thus, the diameter of the axial cavity must be relatively small, and, consequently, the diameter $D_2$ of the measurement means must be smaller. Strength tests were performed for a tool holder made of a standard material whose strength was 550 megapascals (MPa) (=80,000 pounds per square inch (psi)), and whose eccentric segment diameter $D_1$ was about 148.6 millimeters (mm) (=5.85 inches (")), under conditions close to those which apply to a tool holder when used down a well that passes through at least one deposit of fluid, namely: differential pressure between the inside and the outside of the tool holder of about 40 MPa (6,000 psi), and hydrostatic pressure of the fluid flowing through the tool holder of about 103 MPa (15,000 psi). Under those conditions, the tests show that good tool holder strength is obtained for a diameter $D_2$ of the measurement means of about 31.8 mm (1.25") when the axial cavity 3 is not bored where the thickness of the eccentric segment 2 is at its maximum, but rather it is offset at an angle of about 30°, as shown in FIG. 1b, this offset being to make it simpler to install the measurement means, as explained in more detail with reference to FIG. 2. Under such conditions, the length of the oblong radial bore 4 was about 140 mm, which corresponds to the standard length of a scintillator crystal of a gamma ray detector unit. Naturally, depending on the material and on the geometrical characteristics of the tool holder, the dimensions of the measurement means, and thus of the cavity and the openings, may be modified insofar as the tool holder is strong enough to withstand the conditions of use that prevail down an oil well.

With Reference to FIG. 1c:

The embodiment shown in FIG. 1c is identical in its principle to the embodiment shown in FIGS. 1a and 1b, and it thus makes it possible to bring the measurement means closer to the fluid flowing through the body of the tool holder, in order to reduce the noise that interferes with measurements obtained with tool holders known from the state of the art.

However, in this case, the measurement means are not inserted from the outside of the tool holder, but rather they are inserted from inside said tool holder. This solution suffers from the drawbacks of making it more difficult to access the measurement means and more awkward to install them because an installation tool must be used to put the measurement means into the body of the tool holder 1, and then to position them in the axial cavity 3. In this embodiment, the measurement means are installed tangentially to the inside diameter of the tool holder. An axial cavity 3 is bored that is of diameter smaller than the diameter of the axial cavity 3 in the solution described with reference to FIGS. 1a and 1b. However, since the measurement means are brought even closer to the fluid to be characterized, it is possible to increase the diameter $D_2$ of said means. It is also possible to increase significantly the dimensions of the radial opening 4. This results in a larger area in contact with the fluid, and thus in the possibility of using detection means that are larger (and therefore more accurate). This solution does not weaken the tool holder. Indeed, placing the measurement means in the tool holder makes it possible to increase the thickness of the stopper 6 (when the radial opening 4 is bored from the outside wall of the tool holder) and thus to increase the overall strength. Thus, tests performed under the same conditions as those described above with reference to FIGS. 1a and 1b have shown that the strength of the tool holder is satisfactory for measurement means having a diameter $D_2$ of about 35 mm (1.37") bored at about 30° from the maximum thickness of the eccentric segment 2.

In the same way as in the preceding embodiment, a radial opening 5 is bored diametrically opposite the axial cavity 3, said radial openings serving in particular for receiving the source of a source unit, as explained below. A stopper 7 may be positioned over the radial opening 5, and windows made of a material offering low gamma ray attenuation may be installed on the inside wall of the tool holder, closing the openings 4 and 5.

A measurement device 8 of the invention is described in detail below, with reference to FIGS. 2 and 2a, said device being provided with a tool holder as in the embodiment shown in FIGS. 1a and 1b.

The body of the measurement device, which body is constituted by a tool holder of the invention, constitutes a segment of tubing lowered down into a well that passes through at least one deposit of fluid to be characterized, said fluid flowing inside said tubing. As shown in FIG. 2, the measurement device 8 makes it possible to characterize the density and the multi-phase ratio of the fluid coining from the deposit, said fluid usually being constituted by water, hydrocarbons, and gas. For this purpose, the tool holder 1 of the device 8 receives a source unit 9 making it possible to send gamma rays through the fluid, and a detector unit 10 comprising firstly a scintillator crystal 10a for measuring the attenuation of the rays after they have passed through the fluid, and secondly an acquisition unit 10b for processing the count signal transmitted by the scintillator crystal.

As shown in detail in FIG. 2a, the source unit 9 is received entirely in the radial opening 5 which opens out in the inside wall of the tool holder 1. Thus, the source emitting the gamma rays is directly in contact with the multi-phase fluid, which considerably reduces the attenuation of the rays on emission. In addition, this configuration makes it easy to install the source unit 9 in the opening 5 from the outside of the tool holder. Finally, when the multi-phase fluid also flows between the walls of the well and the outside walls of the tool holder without going through the device of the invention, sealing between the inside and the outside of the tool holder is provided, e.g. by welding the stopper 7 of the source unit in the opening 5, which is very easy and inexpensive.

The detector unit 10 is received facing the source unit 9. In practice, the acquisition unit 10b is received in the axial cavity 3, as is the scintillator crystal 10a. Said crystal is further situated where the first radial opening 4 intercepts said axial cavity. In this way, the scintillator crystal is also in direct contact with the fluid to be characterized, and it receives the gamma rays after attenuation, with interference attenuation being minimized.

As shown in FIG. 2, electronic communications and power supply means 11 situated on the outside wall of the tool holder 1, outside the eccentric segment 2, are connected to the acquisition unit 10b. Since the position of the electronic means 11 on the outside wall of the tool holder 1 is induced by the position of relay elements (not shown) along the other segments of the tubing, said electronic means 11 can find themselves offset relative to the maximum thickness of the eccentric segment 2, as is shown in FIG. 2. As a result, in order to position the detector unit in alignment with the electronic means, the axial cavity is not bored in the maximum thickness of the eccentric segment 2, but rather it is offset therefrom, as described above, by an angle of about 30°. Naturally, it is possible to consider having an angular offset between the axial cavity and the position of the electronic means, in particular, for example, so as to bore said cavity in the maximum thickness of the eccentric segment. Such an offset would make it possible to increase the diameter of the axial cavity 3. Tests conducted under the same conditions as those described above have shown that it is possible to obtain good tool holder strength for a diameter $D_2$ that is slightly greater than 31.8 mm for the embodiment shown in FIGS. 1a and 1b and about 36 mm for the embodiment shown in FIG. 1c.

Such a configuration would however assume that the link means 12 between the detector unit and the electronic means are provided with bends, which would complicate installing the measurement device 8. It is 13 also necessary to seal said link. Thus, when the electronic means 11 are in alignment with the detector unit 10, the link 12 can be sealed merely by means of a sealed single metal/metal connection with conical contact at the electronic means, and by annular gaskets at the axial cavity 3. In contrast, an angular offset between the detector unit and the electronic means, requiring link means 12 provided with bends, would make it necessary for two metal/metal connections to be present in order to provide overall sealing: both at the detector unit end and at the electronic means end. For this purpose, the positioning of the detector unit 10 in alignment with the electronic means 11 is preferred.

Finally, in the embodiment shown in FIG. 2, the measurement device 8 further comprises means for mixing the phases of the fluid, so that the measurement means for measuring the density and the multi-phase ratio operate properly. In an advantageous embodiment, these mixing means also make it possible to measure the flow rate of the multi-phase fluid. For this purpose, the device comprises in particular pressure sensors (known and not shown for reasons of clarity), and a venturi 13 positioned inside the tool holder 1 by means of a fastening device 14 known from the sate of the art. In which case, it is the venturi 13 which performs the function of mixing the phases of the multi-phase fluid. As can be seen in FIG. 2, it is important for the fastening device 14 to be dimensioned and/or positioned so that it is not extended to the point of being placed between the source unit 9 and the scintillator crystal 10a, which would result in losing the advantage of positioning these two elements directly in contact with the fluid. In the embodiment of the tool holder of FIG. 1c, where the contact area between the scintillator crystal and the fluid is larger, it is necessary to make provision for cutouts to be formed in the fastening device so that the source unit and the crystal can face each other unobstructed. This makes the embodiment shown in FIG. 1c less practical than the embodiment of FIGS. 1a and 1b because it is particularly difficult to position such cutouts and openings correctly (since the manipulation is performed from the surface).

Naturally, in order to enable other measurement means to be lowered down inside the tubing of which the device 8 constitutes a segment, the measurement means for measuring the flow rate can be easily removed using techniques known from the state of the art.

Figure 3:
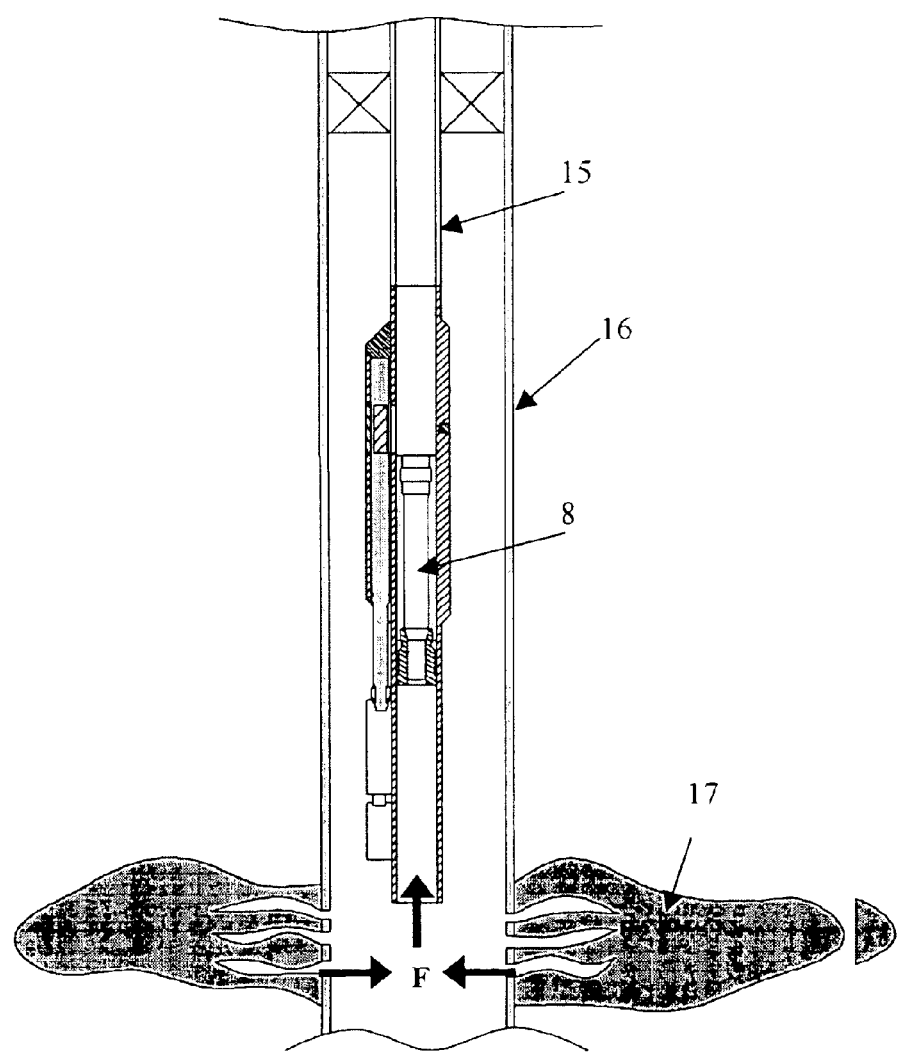
FIG. 3 is an example of the use of a device for characterizing a fluid as shown in FIG. 2.

FIG. 3 shows an embodiment of a measurement device 8 of the invention. Tubing 15 is lowered down a well 16 passing through at least one petroleum deposit 17. The tubing 15 is made up of a plurality of segments, one of which is constituted by the measurement device 8. The fluid coming from the deposit 17 penetrates into the device 8 as indicated by the arrows F, and the above-described measurement means make it possible to determine its density and/or its flow rate. The simplicity of the measurement device of the invention and the possibility of accessing the measurement means as a result of their configuration in the tool holder makes it possible to install said device permanently down the well, with maintenance posing no particular problem.

What is claimed is:

1. A tool holder serving to receive measurement means for characterizing a multi-phase fluid coming from a deposit through which at least one well passes, and flowing inside said tool holder, wherein said tool holder comprises:
    an axial cavity and a first radial opening which opens out in the inside wall of the tool holder and intercepts said axial cavity, said cavity and said opening being adapted to receive said measurement means; wherein said tool holder is cylindrical in shape with a portion of the length of the cylinder being provided with an eccentric segment in which the axial cavity and the first radial opening are bored.

2. A tool holder according to claim 1, wherein said tool is cylindrical in shape with a portion of the length of the cylinder being provided with the integral eccentric segment.

3. A tool holder according to claim 1, wherein the first radial opening also opens out in the outside wall of the tool holder and is sealed off by a stopper situated on said outside wall.

4. A tool holder according to claim 1, wherein the outside wall of said tool serves to receive electronic communications and power supply means connected to the measurement means.

5. A tool holder according to claim 1, further composing second radial opening which opens out in the inside wall of the tool holder and is diametrically opposite from the first radial opening.

6. A tool holder according to claim 5, wherein the first radial opening also opens out in the outside wall of the tool holder, and is sealed off by a stopper situated on said outside wall.

7. A tool holder according claim 6, wherein the outside wall of said tool serves to receive electronic communications and power supply means connected to the measurement means.

8. A tool holder according to claim 7, wherein said tool is cylindrical in shape with a portion of the length of the cylinder being provided with the integral eccentric segment.

9. A device for characterizing a multi-phase fluid coming from a deposit through which at least one well passes, said device comprising:
    a source unit for emitting gamma rays through said multi-phase fluid;
    a detector unit having a scintillator crystal receiving said gamma rays after they have passed through the fluid; and
    a tool holder comprising an axial cavity and a first radial opening which opens out in the inside wall of said tool holder and intercepts said axial cavity; such that the detector unit is positioned in the axial cavity of said tool holder so that the scintillator crystal is situated in the first radial opening in said tool holder.

10. A device according to claim 9, wherein the outside wall of the tool holder serves to receive electronic communications and power supply means connected to the source unit and the detector unit.

11. A device according to claim 9 wherein the tool holder is cylindrical in shape with a portion of the length of said cylinder being provided with an eccentric segment in which the axial cavity and the first radial opening are bored.

12. A device according to claim 9, wherein the first radial opening of the tool bolder also opens out in the outside wall of said tool holder, and is sealed off by a stopper situated on said outside wall.

13. A device according to claim 9, wherein the first radial opening of the tool holder is an oblong opening whose dimensions correspond to the dimensions of the scintillator crystal.

14. A device according to claim 13, wherein the tool holder further comprises a second radial opening which opens out in the inside wall said tool holder and is diametrically opposite from the first radial opening.

15. A device according to claim 14 wherein the source unit is situated in the second radial opening in the tool holder.

16. A device according to claim 15, further comprising means for determining the flow rate of the multi-phase fluid, said means being fixed to the tool holder upstream from the detector unit and from the source unit.

17. A device according to claim 16, wherein said device constitutes a segment of tubing that is lowered and fixed permanently down the well passing through the deposit of multi-phase fluid.

18. A device according to claim 17, wherein the first radial opening of the tool holder also opens out in the outside wall of said tool holder, and is sealed off by a stopper situated on said outside wall.

19. A device according to claim 18, wherein the outside wall of the tool holder serves to receive electronic communications and power supply means connected to the source unit and the detector unit.

20. A device according to claim 19 wherein the tool holder is cylindrical in shape with a portion of the length of said cylinder being provided with an eccentric segment in which the axial cavity and the first radial opening are bored.

* * * * *

UNITED STATES PATENT AND TRADEMARK OFFICE
CERTIFICATE OF CORRECTION

PATENT NO. : 6,915,685 B2
DATED : July 12, 2005
INVENTOR(S) : Emmanuel Fayeulle et al.

It is certified that error appears in the above-identified patent and that said Letters Patent is hereby corrected as shown below:

<u>Title page,</u>
Item [75], Inventors, add -- Vincent Tourillon, Paris, France. --.

Signed and Sealed this

Fourth Day of April, 2006

JON W. DUDAS
*Director of the United States Patent and Trademark Office*